(12) United States Patent
Enders

(10) Patent No.: US 8,653,324 B2
(45) Date of Patent: Feb. 18, 2014

(54) TETO-P16 TRANSGENIC MICE

(75) Inventor: Greg H. Enders, Villanova, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 131 days.

(21) Appl. No.: 13/157,477

(22) Filed: Jun. 10, 2011

(65) Prior Publication Data

US 2011/0307967 A1    Dec. 15, 2011

Related U.S. Application Data

(60) Provisional application No. 61/353,824, filed on Jun. 11, 2010.

(51) Int. Cl.
*A01K 67/027* (2006.01)
*C12N 15/90* (2006.01)
*C12N 15/873* (2010.01)

(52) U.S. Cl.
USPC ............. 800/18; 800/21; 800/22; 800/25

(58) Field of Classification Search
USPC .......................... 800/18, 21, 22, 25
See application file for complete search history.

(56) References Cited

U.S. PATENT DOCUMENTS 5,919,997 A * 7/1999 Beach et al. ............ 800/18
2012/0004277 A1 * 1/2012 Arendt et al. ........... 514/44 A

FOREIGN PATENT DOCUMENTS

WO    WO 2005/068659    * 7/2005

OTHER PUBLICATIONS

Sun et al. (2007) Acta Biochim. Biophys. Sinica, vol. 39(4), 235-246.*
Squence alignment between SEQ ID No. 1 of Lubinski et al. and SEQ ID No. 14.*
Barker N., et al., Identification of stem cells in small intestine and colon by marker gene Lgr5., Nature, Oct. 2007, vol. 449, pp. 1003-1007.
Clapper ML, et al., Dextran sulfate sodium-induced colitis-associates neoplasia: a promising model for the development of chemopreventive interventions, Acta Pharmacol. Sin., 2007, vol. 28, pp. 1450-1459.
Dai CY, et al., p16(INK4a) expression begins early in human colon neoplasia and correlates inversely with markes of cell proliferation, Gastroenterology, Oct. 2000, vol. 119, pp. 929-942.
Dai CY, et al., p16INK4a can initiate an autonomous senscence program, Oncogene, 2000, vol. 19, pp. 1613-1622.
Diaz-Rodriguez E., et al., Hec1 overexpression hyperactivates the mitotic checkpoint and induces tumor formation in vivo, Proc. Natl. Acad. Sci. USA, 2008, vol. 105, pp. 16719-16724.
Gossen M., et al., Tight control of gene expression in mammalian cells by tetracycline-responsive promoters, Proc. Natl. Acad. Sci. USA, 1992, vol. 89, pp. 5547-5551.
Mitra J., et al., Induction of p21WAF1/CIP1 and Inhibition of Cdk2 Mediated by the Tumor Supressor p16INK4a, Mol. Cell Biol, 1999, vol. 19, No. 5, pp. 3916-3928.
NCBI Reference Seq.: NM_000077.4.
NCBI Reference Seq.: NM_058197.3.
Serrano M., et al., A new regulatory motif in cell-cycle control causing specific inhibition of cyclin D/CDK4, Nature, 1993, 366(6456): 704-7.

* cited by examiner

*Primary Examiner* — Anne Marie S Wehbe
(74) *Attorney, Agent, or Firm* — Stradley Ronon Stevens & Young, LLP

(57) ABSTRACT

Mice comprising a human p16 transgene operably linked to an inducible promoter and capable of controlled expression of p16 are provided. Also provided are cells, tissues, and organs obtainable from such mice, and methods for producing p16 transgenic mice.

23 Claims, 20 Drawing Sheets
(17 of 20 Drawing Sheet(s) Filed in Color)

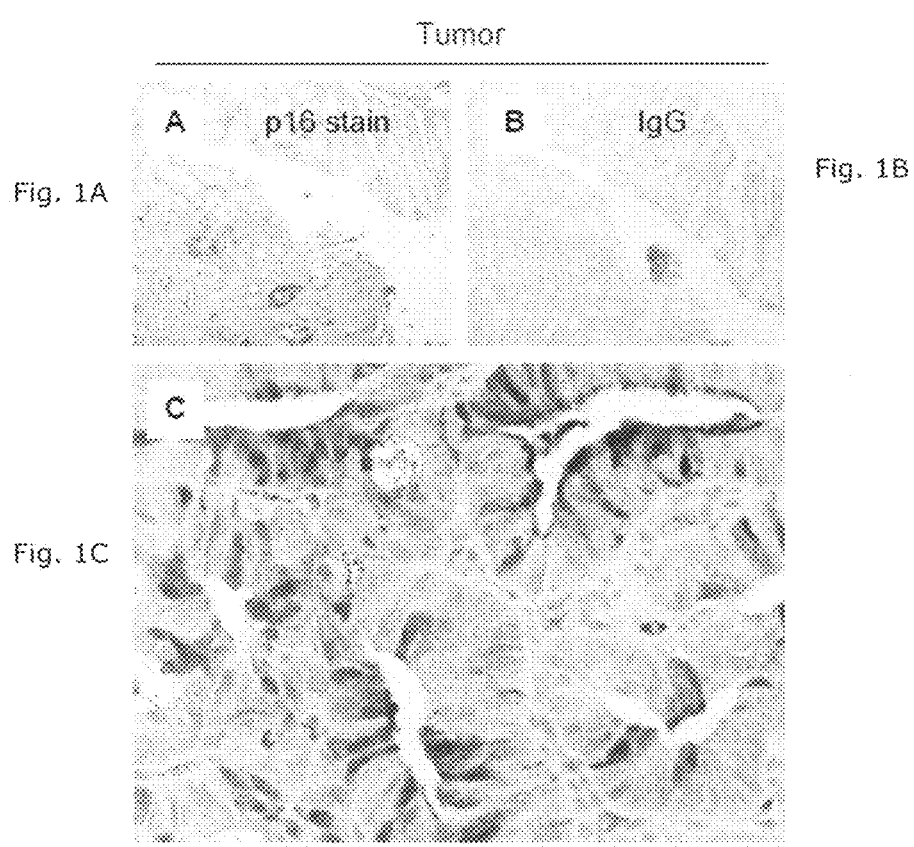

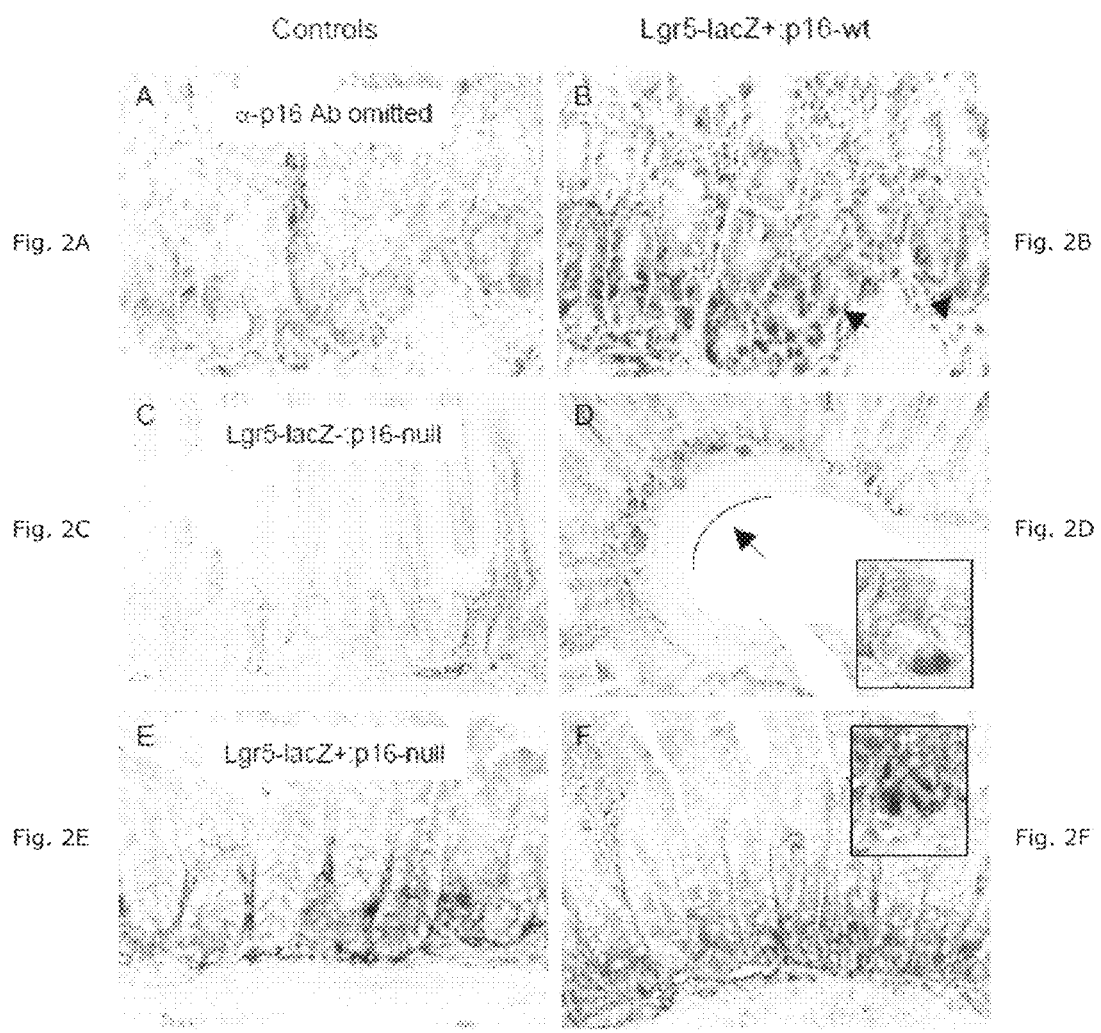

Fig. 11A
Fig. 11B
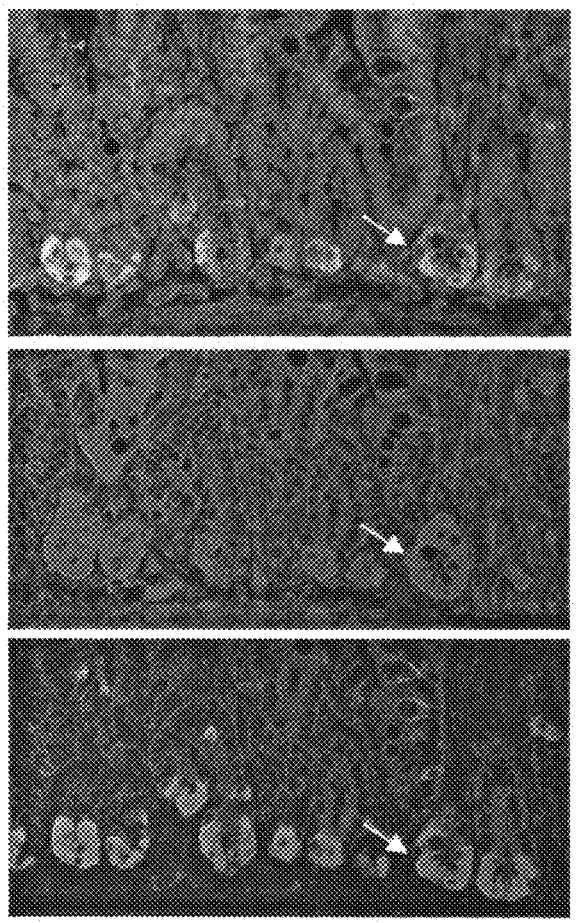
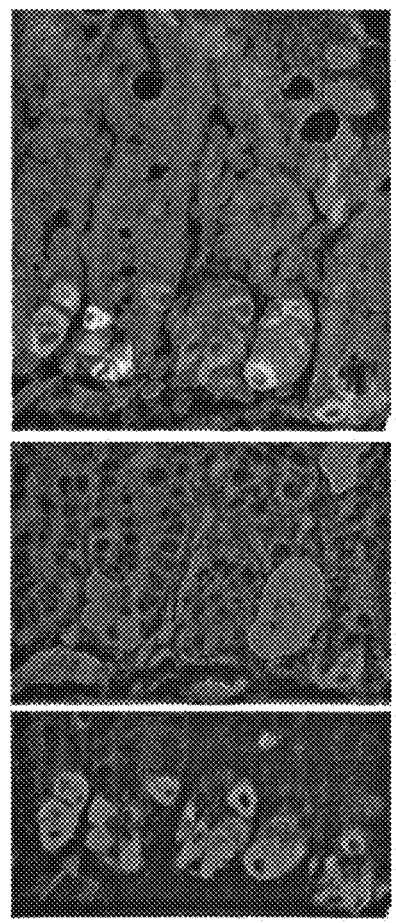

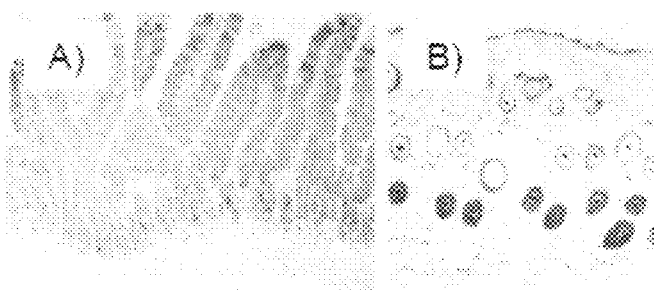
Fig. 14A
Fig. 14B
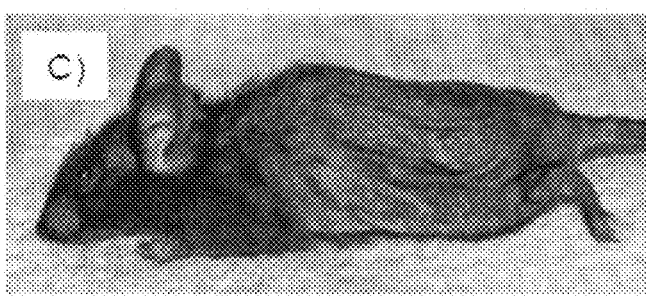
Fig. 14C

TETO-P16 TRANSGENIC MICE

CROSS REFERENCE TO RELATED APPLICATION(S)

This application claims priority to U.S. Provisional Application No. 61/353,824 filed on Jun. 11, 2010, the entire contents of which are incorporated by reference herein, in their entirety and for all purposes.

STATEMENT OF GOVERNMENT SUPPORT

The inventions described herein were made, in part, with funds obtained from the National Institutes of Health, Grant No. R01 DK64758. The U.S. government may have certain rights in these inventions.

REFERENCE TO A SEQUENCE LISTING

This application includes a Sequence Listing submitted electronically as a text file named TetO-p16 NP Sequence Listing_ST25.txt, created on Jun. 6, 2011, with a size of 8,000 bytes. The Sequence Listing is incorporated by reference herein.

FIELD OF INVENTION

The invention relates generally to the field of molecular biology. More particularly, the invention relates to mice comprising a p16(lnk4a) transgene operably linked to an inducible promoter, as well as cells, tissues, and organs obtainable from such mice, and methods for producing such mice.

BACKGROUND OF THE INVENTION

Various publications, including patents, published applications, accession numbers, technical articles and scholarly articles are cited throughout the specification. Each cited publication is incorporated by reference herein, in its entirety and for all purposes.

The tumor suppressor p16lnk4a mediates cell cycle arrest and senescence in vitro, constrains proliferation of some aging progenitors cells, and is widely used as a marker of cellular senescence and aging in vivo. However, whether p16 expression is sufficient to confer cell cycle arrest, senescence, or aging features in vivo is unknown.

Induction of p16 in tumors arising in situ can test whether inhibition of its target cyclin dependent kinases (cdk) can block growth of such tumors. Cdk inhibitors are being broadly developed by the pharmaceutical industry for cancer chemotherapy. However, whether inhibition of cdks can block tumor growth is unknown.

p16lnk4a has been known to the research community for nearly 20 years, but a p16-inducible mouse has not previously been generated. On the one hand, some published data questions whether p16 would block growth of cells in the animal. On the other hand, prior to the experiments described herein, it might have been expected that mice with p16 induction would die promptly, making them unsuitable for many experiments.

There is a need to produce p16 transgenes with an inducible activator expressed in a tissue-specific fashion to avoid potential morbidity and mortality from p16 expression.

SUMMARY OF THE INVENTION

The invention features a transgenic mouse comprising a transgene comprising a nucleic acid sequence encoding human p16(lnk4a) operably linked to an inducible promoter. The transgene preferably is stably integrated into the mouse genome, for example, into a chromosome. The inducible promoter may be activated by the reverse tetracycline-controlled transactivator.

Upon induction of the transgene, the human p16(lnk4a) is expressed. Preferably, the expression occurs in a cell, tissue, or organ of interest. The cell, tissue, or organ may include the skin, tongue, esophagus, stomach, intestine, or other organ. Cells, tissues, or organs comprising the transgene may be isolated from the mouse.

The invention also features methods for producing a transgenic mouse. In some aspects, the methods generally comprise introducing a nucleic acid sequence encoding human p16(lnk4a) operably linked to an inducible promoter into a mouse egg, embryo, or embryonic stem cell, and transferring the mouse egg, embryo, or embryonic stem cell having the introduced nucleic acid sequence into a female mouse. The p16 nucleic acid sequence may be operably linked to an operon capable of activation by the reverse tetracycline transactivator, including a multimeric operon. The methods may comprise breeding the female mouse and selecting offspring having the nucleic acid sequence.

In some aspects, the methods generally comprise introducing a nucleic acid sequence encoding human p16(lnk4a) into a mouse egg, embryo, or embryonic stem cell, transferring the mouse egg, embryo, or embryonic stem cell having the introduced nucleic acid sequence into a female mouse, breeding the female mouse with a male mouse comprising a reverse tetracycline transactivator transgene, and selecting offspring having the nucleic acid sequence and the reverse tetracycline transactivator transgene. The nucleic acid sequence is preferably operably linked to an operon capable of activation by the reverse tetracycline transactivator, including a multimeric operon.

Animals produced by the inventive methods are also included.

The invention also features methods for inducing p16 expression in a transgenic mouse. Generally, the methods comprise administering an agent capable of activating an inducible promoter operably linked to the p16 transgene to the mouse. Preferably, the inducible promoter is the reverse tetracycline controlled transactivator, and the agent is tetracycline (tet) or a tetracycline analog such as doxycycline. The agent may be selectively administered to a tissue of interest.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows preferential p16 expression in Lgr5-lacZ+ intestinal stem cells. Immunohistochemical staining was performed for p16 (brown, mainly nuclear; arrows, inserts) in Lgr5-lacZ+ transgenic mouse small intestine co-stained for lacZ by activity assay (aqua, largely cytoplasmic; B, D, F) and negative controls (A, C, E). Note the preferential staining for p16 in Lgr5+ crypt cells. Note lack of p16 staining in: (A) Non-specific IgG used instead of p16 antibody. C) p16-null mouse lacking Lgr5-lacZ transgene, and E) Lgr5-lacZ+:p16-null mouse. Images A, B, E, F: 20×, B,D: 10×.

FIG. 3 shows patchy spontaneous alopecia in TetO-p16 mice.

FIG. 5 shows p16 induction in CMV-rtTA:TetO-p16 mice inhibits intestinal epithelial cell proliferation.

FIG. 7 shows induced p16 inhibits Lgr5-lacZ+ intestinal stem cell proliferation.

FIG. 11 shows increased co-staining of p16 and the paneth cells marker lysozyme over weeks by confocal co-IF.

FIG. 12 shows Dox withdrawal allows recovery of aging features. CMV-rtTA:TetO-p16 mice were treated with Dox d20-40 and divided into 2 groups. Dox was sustained in the first group and withdrawn in the second group and mice were sacrificed and characterized at d80.

FIG. 14 shows p16 induction in M2-rtTA:TetO-p16 mice causes pre-mature aging features.

DETAILED DESCRIPTION OF THE INVENTION

Figure 1D:
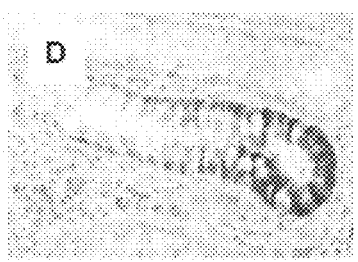
FIG. 1 shows endogenous p16 is induced in colitis and intestinal tumors.
Figure 1E:
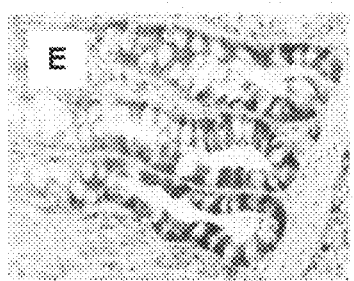
Figure 1F:
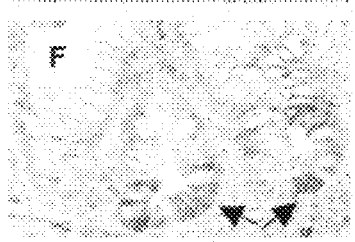

Various terms relating to aspects of the invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The term "operably linked" means that the regulatory sequences are placed in the appropriate location, position, arrangement, and/or orientation relative to the coding sequence of interest so as to enable expression of the coding sequence. In one non-limiting example, a promoter is operably linked with a coding sequence when the promoter is capable of controlling the transcription or expression of that coding sequence.

"Promoter" refers generally to regulatory elements of a gene, which may be found upstream or downstream of the coding region, within the coding region itself, or within introns.

It has been observed in accordance with the invention that viable TetO-p16 transgenic mice could be produced, that these mice allow inducible expression of a potent cell cycle inhibitor, p16Ink4a, and that p16 expression inhibited cell proliferation in each of the tissues studied. The p16(Ink4a) sequence used was the original cDNA described and characterized in Serrano et al. Nature 366:704-707 (1993). This sequence starts at nucleotide 237 of the new NCBI reference standard NM_058197.3 (SEQ ID NO:15).

The invention features p16 transgenic mice. The mice allow broad control of cell proliferation in the mice, and they may be useful as a tool to aid studies of development, tissue renewal, aging, cancer, and a variety of chronic diseases that involve cell proliferation.

In one aspect, a transgenic mouse comprises a transgene comprising a nucleic acid sequence encoding human p16 (Ink4a), preferably operably linked to an inducible promoter. Any inducible promoters capable of use in transgenic mice that are known in the art may be used in the transgenic mice of the invention. Non-limiting examples include Cre/lox, estrogen, glucocorticoid, and ecdysone inducible promoters, antibiotic inducible promoters such as macrolide and tetracycline controlled promoters, and beta-napthoflavone. Tetracycline systems, including the tetracycline controlled transactivator and derivatives thereof are preferred, with the reverse tetracycline-controlled transactivator being highly preferred.

The mice comprise at least one copy of the transgene, which preferably is stably integrated into a chromosome. The transgene may be present in the gametes and/or somatic cells of the animal. The transgene may comprise SEQ ID NO:14. The transgene may comprise nucleic acids 233-683 of SEQ ID NO:13, or nucleic acids 233-683 of accession number NM_000077.

Preferably, the transgene is present in and capable of expression in one or more tissues or organs in the mouse upon induction. Exemplary tissues and organs include, but are not limited to, the skin, tongue, bone marrow, and muscle tissues of the gastrointestinal tract such as the esophagus, stomach, small intestine, and large intestine. Cells, tissues, or organs comprising the transgene may be isolated from the mouse, and may be grown in culture and/or subjected to further study.

It is possible to achieve tissue-specific (and organ-specific) expression of the transgene, for example, by inducing the transgene in the tissue of interest. Induction may be carried out by administering an inducing agent directly to or at least in the proximity of the tissue of interest. For example, the transgene may be induced by administering an inducing agent via the animal's food or water supply. The inducible agent may be administered in the blood or other biological fluid (e.g., cerebrospinal fluid), and may be actively targeted to the tissue of interest, for example, by using carriers, liposomes, antibodies, and/or magnets. Local expression of the transgene may be achieved by local application of an inducer, such as by application to the skin or inhalation of a mist in the lungs. Any suitable route or technique to administer the agent may be used, and may vary, for example, according to the needs of the investigator or according to the characteristics of the agent itself. Although the inducing agent may achieve systemic exposure upon administration, induction in specific cells, tissues, or organs of interest to the exclusion of others may be controlled by way of particular regulatory elements in the transgene. Alternatively, tissue or cell-specific expression of the transgene may be achieved by mating the mice with mice that express the transactivator in restricted tissues or cell types.

The invention is not limited to mice, and can include any member of a category of other non-human mammals such as rodents (e.g., rats, rabbits), companion animals, farm animals, non-human primates, and other non-human mammals. Mice, being exemplified, are preferred.

The invention also features methods for producing a transgenic mouse, as well as mice produced by any of the methods. In some aspects, the method comprises breeding a mouse comprising a p16(lnk4a) transgene with a mouse comprising a reverse tetracycline transactivator transgene, and selecting offspring having the p16(lnk4a) transgene and the reverse tetracycline transactivator transgene.

In some aspects, the method comprises introducing a nucleic acid sequence encoding human p16(lnk4a) operably linked to an inducible promoter into a mouse egg (fertilized or unfertilized), zygote, embryo, or embryonic stem cell, and transferring the mouse egg, zygote, embryo, or embryonic stem cell having the introduced nucleic acid sequence into a female mouse. The method may further comprise fertilizing the egg. The method may further comprise breeding the female mouse and selecting offspring having the nucleic acid sequence. The inducible promoter may be any suitable promoter, including those described or exemplified herein. In some aspects, the p16 nucleic acid sequence may be operably linked to an operon capable of being activated by the reverse tetracycline transactivator, including a multimeric operon. Offspring may be referred to as "potential founders."

In some aspects, the methods comprise breeding a potential founder mouse and their progeny carrying a p16 transgene with a mouse comprising a reverse tetracycline transactivator transgene, and selecting offspring having the p16 nucleic acid sequence and the reverse tetracycline transactivator transgene.

In some aspects, the method comprises introducing a nucleic acid sequence encoding human p16(lnk4a) into a mouse egg (fertilized or unfertilized), zygote, embryo, or embryonic stem cell, transferring the mouse egg, zygote, embryo, or embryonic stem cell having the introduced nucleic acid sequence into a female mouse, breeding the female mouse with a male mouse comprising a reverse tetracycline transactivator transgene, and selecting offspring having the nucleic acid sequence and the reverse tetracycline transactivator transgene. The nucleic acid sequence may be operably linked to an operon capable of activation by the reverse tetracycline transactivator. The operon may be a single or a multimeric operon.

Any technique suitable for introducing the nucleic acid sequence may be used. Non-limiting examples include electroporation, microinjection, viruses, lipofection, calcium phosphate, and other known transformation techniques.

Animals, including offspring, may be screened to confirm the presence of the transgene according to any technique suitable in the art. For example, cells may be isolated and tested for the presence of the gene, a detectable marker, selection marker, translation product, detectable mRNA, and/or detectable phenotype.

Offspring carrying the transgene can further be bred with other animals to perpetuate the transgenic line, or can be bred with animals carrying other transgenes. Breeding includes back crossing, including back crossing into distinct genetic backgrounds. Offspring include any filial or backcross generation.

The following examples are provided to describe the invention in greater detail. They are intended to illustrate, not to limit, the invention.

EXAMPLE 1

General Experimental Methods

A. Transgenic Mice.

Figure 15:
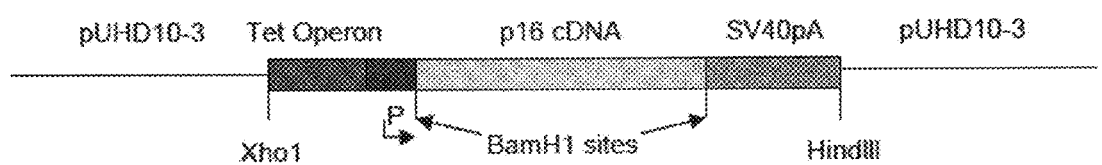
FIG. 15 shows a TetO-p16 transgene structure.

TetO-p16 mice were generated by standard pro-nuclear injection of a p16 transgene derived from plasmid pUH10-3 (Gossen M et al. (1992) Proc. Natl. Acad. Sci. USA 89:5547-51). In this construct, the human p16 cDNA, matching sequences 233 through 683 (SEQ ID NO:14) of GenBank NM_000077 (SEQ ID NO:13), was cloned behind a tetracycline operon/minimal promoter, using the BamH1 site in the polylinker. This construct has been extensively validated previously (Mitra J et al. (1999) Mol. Cell Biol. 19:3916-28; and Dai C Y et al. (2000) Oncogene 19:1613-22). For injection, the transgene was liberated by digestion with XhoI and HindIII restriction enzymes. FIG. 15 shows a representation of the transgene.

Founder mice and transgene-carrying progeny were identified by PCR of tail DNA using the primers AGCTCGTT-TAGTGAACCGTCA (forward, in promoter sequences) (SEQ ID NO: 11) and CCTCCGACCGTAACTATTCG (reverse, in p16 sequences) (SEQ ID NO:12). These mice were generated in C57Bl/6×C3 genetic backgrounds. These and all other mice were maintained on standard chow and day/night cycles. All animal work was approved by the Institutional Animal Care and Use Committee of Fox Chase Cancer Center.

CMV-rtTA transgenic mice were generated in the laboratory of Harold Varmus (then at Memorial Sloan Kettering Cancer Center (MSKCC), New York, N.Y., U.S.A.; now the National Institutes of Health, Bethesda, Md., U.S.A.) and kindly provided in a C57Bl/6 genetic background by Robert Benezra (MSKCC) (Diaz-Rodriguez E et al. (2008) Proc. Natl. Acad. Sci. USA 105:16719-24.

ROSA M2-rtTA transgenic mice were obtained in a C57Bl/6 genetic background from Jackson Laboratories (stock #006965 B6.Cg-Gt(ROSA)26Sor$^{tm1(rtTA*M2)Jae}$/J, Bar Harbor, Me., U.S.A.). Lgr5-lacZ transgenic mice were obtained in a 129Sv genetic background from Hans Clevers (Vereniging Het Nederlands Kanker Instituut, The Netherlands) and backcrossed twice into a C57Bl/6 genetic background before use. K5-rtTA mice were kindly provided in a BALB genetic background by Jonathan Chernoff (Fox Chase Cancer Center, Philadelphia, Pa., U.S.A.). Multiple intestinal neoplasia (Min) mice in a C57Bl/6 background were obtained from Jackson Laboratories (Bar Harbor, Me.).

Colitis was induced using 4 cycles of dextran sodium sulfate treatment as described (Clapper ML et al. (2007) Acta Pharmacologica Sinica 28:1450-9. Doxycycline treatment was with chow provided by Harlan Laboratories (625 parts per million, Somerville, N.J.). BrdU was injected in the peritoneum (100 µl of a 10 mg/mL solution) 4 h before sacrifice. To shave hair from living animals, mice were anesthetized with inhaled isofluorane. Residual hair was removed by topical application of Nair maximum strength (obtained over the counter in retail pharmacies) for 2 minutes.

B. Immunohistochemistry (IHC), immunofluorescence (IF), and β-galactosidase activity assays in tissue.

IHC and IF were generally performed as described previously (Dai C Y et al. (2000) Gastroenterology 119:929-42. The following antibodies were used: human p16 (K2, kindly provided by Jim Koh, Duke University, Durham, N.C.), mouse p16 (M156, Santa Cruz Biotechnology, Santa Cruz, Calif., U.S.A.) BrdU (IHC: Becton Dickinson, San Diego, Calif., U.S.A. #347580; IF: Abgene, Epsom U.K., Ab1893), activated Caspase 3 (#9661Cell Signaling Technology, Danvers, Mass., U.S.A., lysozyme (Dako, Carpineria, Calif., U.S.A., # EC.3.2.1.17), chromogranin A (Immunostar, Hudson, Wis., U.S.A. #20085). Lgr5-lacZ expression was assayed in tissues by a modification of methods described previously (Barker N et al. (2007) Nature 449:1003-7). Freshly excised tissue was fixed in 0.1% formalin/X for 10 minutes at 4° C., then incubated in X-gal substrate at 4° C. overnight, embedded in paraffin and sectioned.

EXAMPLE 2

Experimental Results

A. Expression of Endogenous Mouse p16 in Intestine Phenocopies the Human Protein and Occurs Preferentially in Stem Cells.

p16 suppresses tumorigenesis in the intestine. This observation together with the intestine's robust proliferation make the intestine a good setting to study p16 expression and effects. Direct evidence for p16 expression in and regulation of progenitor cells remains scant. Knockin mouse lines provide genetically validated markers of intestinal stem cells, providing target cells for study of p16 effects. It was first assessed whether p16 expression in mouse intestine recapitulated patterns observed in human intestine. p16 expression could be detected in mouse intestine by RT-PCR (data not shown).

As for human p16, mouse p16 staining was low in normal epithelium and markedly increased in epithelium of intestinal tumors and colitis (FIG. 1C and FIG. 1D). Such staining was absent in corresponding p16-null tissue (data not shown). Expression was highest as the base of crypts in both non-neoplastic tissue and adenomas, locations of known or suspected stem cells, respectively. To further assess whether p16 was expressed in stem cells of normal intestine of young adults, Lgr5-lacZ knockin mice were examined. Co-staining for IacZ by β-galactosidase activity assay and p16 by immunohistochemistry demonstrated that p16 is preferentially expressed in Lgr5+ stem cells (FIG. 2B, 2D, 2E). Such staining was not seen with non-specific IgG (FIG. 2A) or p16-null mice (FIG. 2C, 2E). Among 6,879 cells scored in 3 mice, p16 staining was detected in 40% of Lgr5+ cells versus 9% of transit-amplifying cells and 1% of villous cells (each comparison to Lgr5+ cells P<0.00001).

B. Generation of Transgenic Mice with Inducible p16 Expression.

To directly test the impact of p16 expression, transgenic mouse lines were generated in which p16 expression can be conditionally expressed (TetO-p16). The human p16 was chosen because it is functionally indistinguishable from mouse p16 in ability to arrest mouse cells in vitro and can be sensitively and specifically detected with the monoclonal antibody JC2. This antibody does not efficiently recognize mouse p16 (data not shown).

A construct in which the p16 cDNA is cloned behind a tetracycline operon was used. It was previously shown that this construct permits robust tetracycline-regulated expression of p16 in vitro. Two founder lines were generated.

Figure 3A:
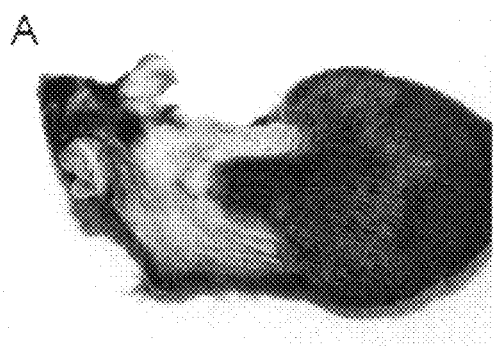
FIG. 3A) TetO-p16-1 founder mouse.
Figure 3B:
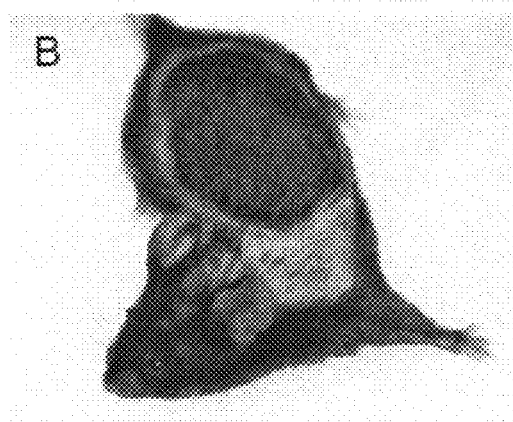
FIG. 3B) F1 progeny of TetO-p16-2 founder mouse. Note the bilateral symmetry.
Figure 4:
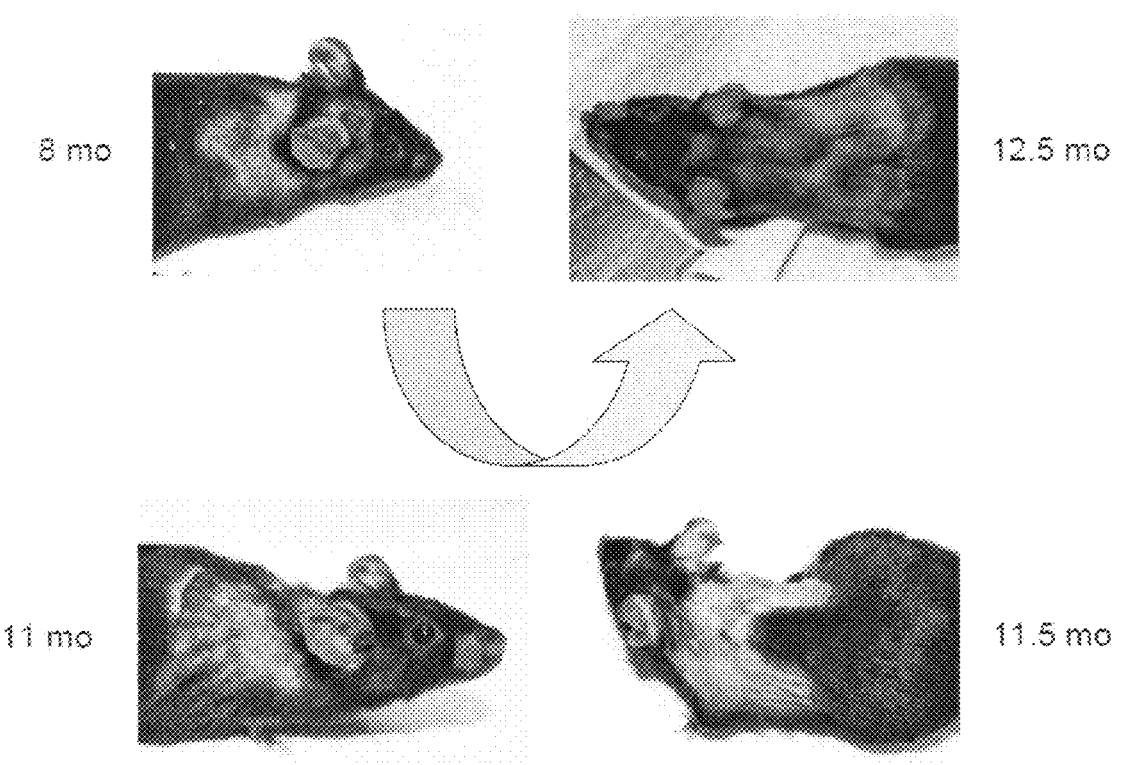
FIG. 4 shows patterns of spontaneous alopecia in TetO-p16 mice. The TetO-p16-1 founder mouse was photographed at intervals from X to X months. Note that the alopecia waxes and wanes but stays in the same general location and gradually expands.

PCR amplification and DNA sequencing of p16 coding regions in each line showed them to be intact (data not shown). TetO-p16 mice were healthy and fertile, but a few developed patches of alopecia around one month, the time of the first wave of hair regeneration (FIGS. 3A and 3B). This phenotype was independent of transgene integration site, because it occurred in both transgenic lines and a third potential founder that was extensively affected and was sterile (data not shown). The patches were typically bilaterally symmetric (FIG. 3B), suggesting that their distribution was determined during embryogenesis and affected subsequent local waves of hair regeneration (FIG. 4). The defects waxed and waned but remained centered over the same site and often expanded (FIG. 4). Leaky spontaneous p16 expression was confirmed in ⅔ affected mice with alopecia (data not shown). This phenotype suggested that p16 expression might be sufficient to block regeneration of hair in young mice.

C. p16 Inhibits Cell Cycle Progression in Epithelial Cells In Vivo.

Figure 5A:
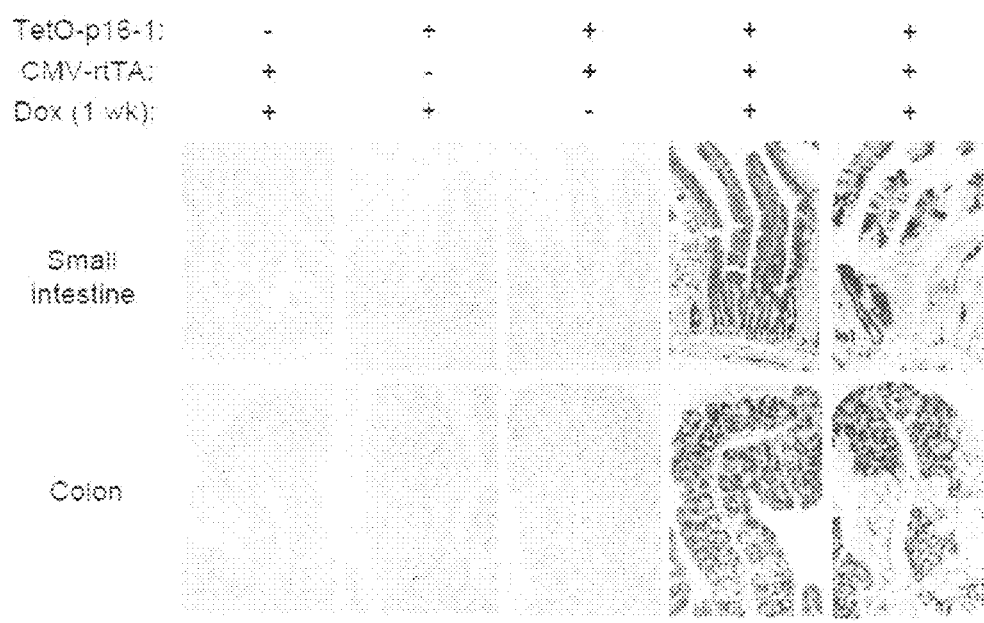
FIG. 5A) Mice of the designated genotypes were or were not treated with Dox for one week, as designated. Jejunum and colon intestinal tissue was subjected to immunohistochemical staining for p16 (brown). Note the robust mosaic p16 induction in the presence of both transgenes and Dox.

To examine p16 regulation in TetO-p16 mice, these mice were mated to transgenic mice that express the reverse tetracycline transactivator from a human cytomegalovirus promoter (CMV-rtTA). Treatment of young CMV-rtTA:TetO-p16 adult (3 month old) mice with Dox for one week broadly and robustly induced p16 in a manner (FIG. 5A). Induction was very similar in the two lines.

These two transgenic lines have been used throughout the following experiments, with indistinguishable results, verifying that these results are independent of the transgene integration site. Induction was, however, mosaic, consistent with previous experience with the CMV-rtTA transactivator. This pattern has the advantage of allowing direct comparison of the behavior of p16-expressing cells to nearly non-expressing cells in the same genetic background and tissue environment. Protein was extracted from intestinal epithelial cells isolated by simple EDTA shake off methods. Immunoblotting (IB) and immunoprecipitation (IP) confirmed that p16 was strongly induced and bound to Cdk4 (data not shown). To assess whether p16 was functional in the transgenic lines, bromodeoxyuridine (BrdU) was injected in the peritoneal cavity 4 h before sacrifice.

Figure 5B:
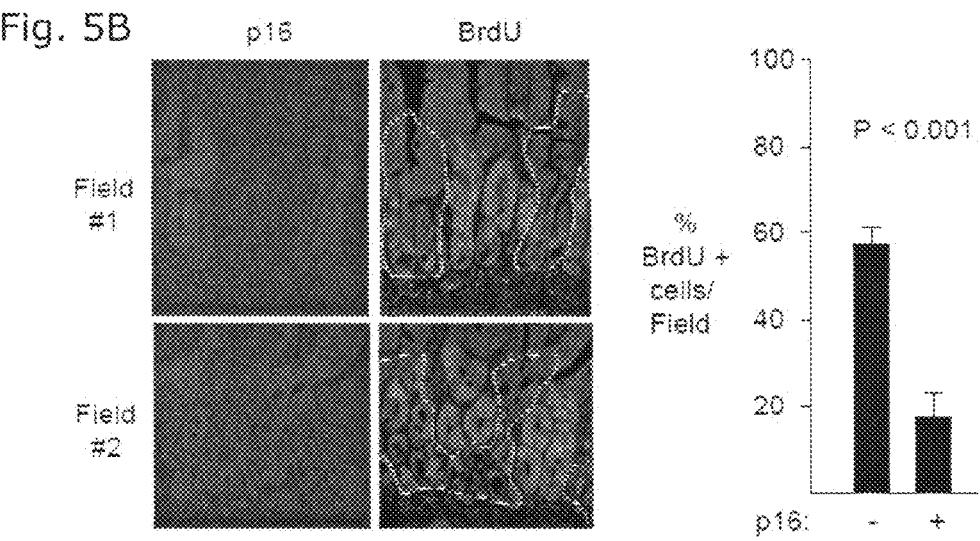
FIG. 5B) CMV-rtTA:TetO-p16 mice were treated with Dox for one week and injected with BrdU 4 h before sacrifice. Co-immunofluorescence (co-IF) for p16 (left, green; outlined by dashed lines in BrdU image) and BrdU (right, red). Among 1122 crypt cells, 19% of p16+ cells were BrdU+ vs. 58% of p16− cells (graph, $P<0.001$ by Chi-squared analysis).

Intestinal tissue was harvested, fixed in formalin, embedded in paraffin, sectioned, and co-stained by indirect immunofluorescence for p16 and BrdU. The results show that p16 induction for one week inhibited BrdU incorporation by about 65% (FIG. 5B, P<0.001). BrdU incorporation and all other features assayed in the following experiments were indistinguishable in wild type or singly transgenic mice so these data were combined (data not shown).

Figure 6A:
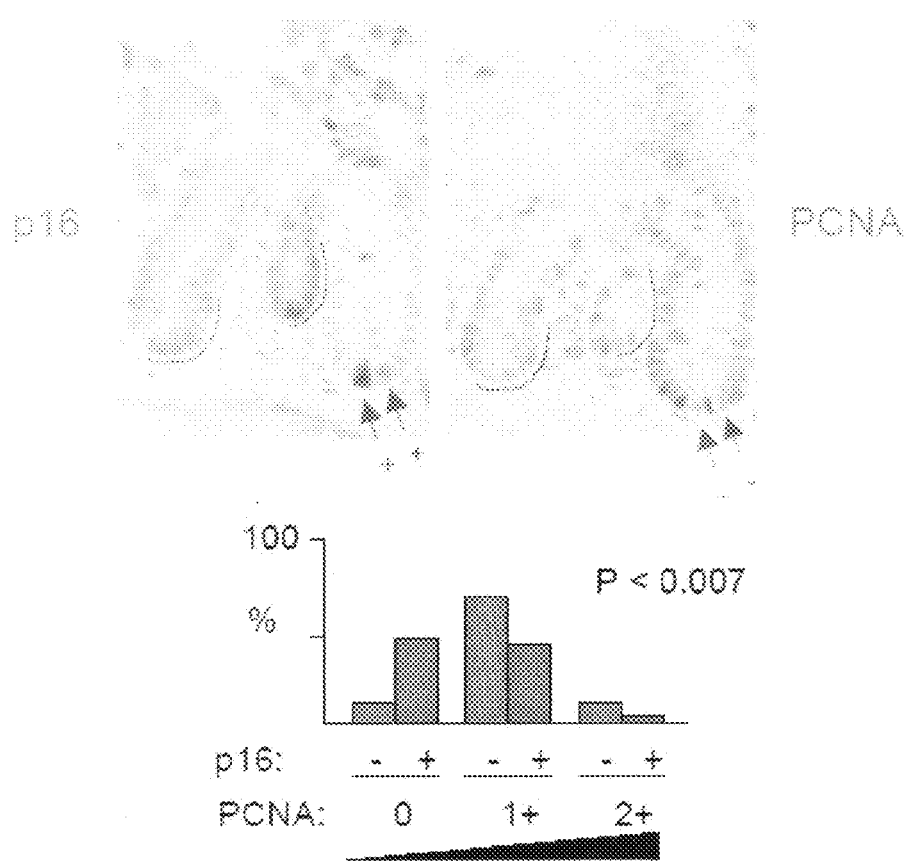
FIG. 6 shows p16 induction blocks intestinal cell proliferation. p16 was induced for 1 wk in CMV-rtTA:TetO-p16 mice. Serial 4-5 micron sections of intestinal tissue were stained for p16 and either PCNA (A) or P-H3 (B). PCNA staining was scored as absent (0), weak (1), or strong (2). Staining in adjacent $p16^+$ and $p16^-$ cells in the same 20×field was scored. P-H3 staining, which was less common and typically occurred in small, rounded cells toward the crypt lumen, was scored per crypt. Crypts were divided into those in which exogenous p16 staining was absent, present in a fraction of crypt cells, or present uniformly in the crypt.
Figure 6B:
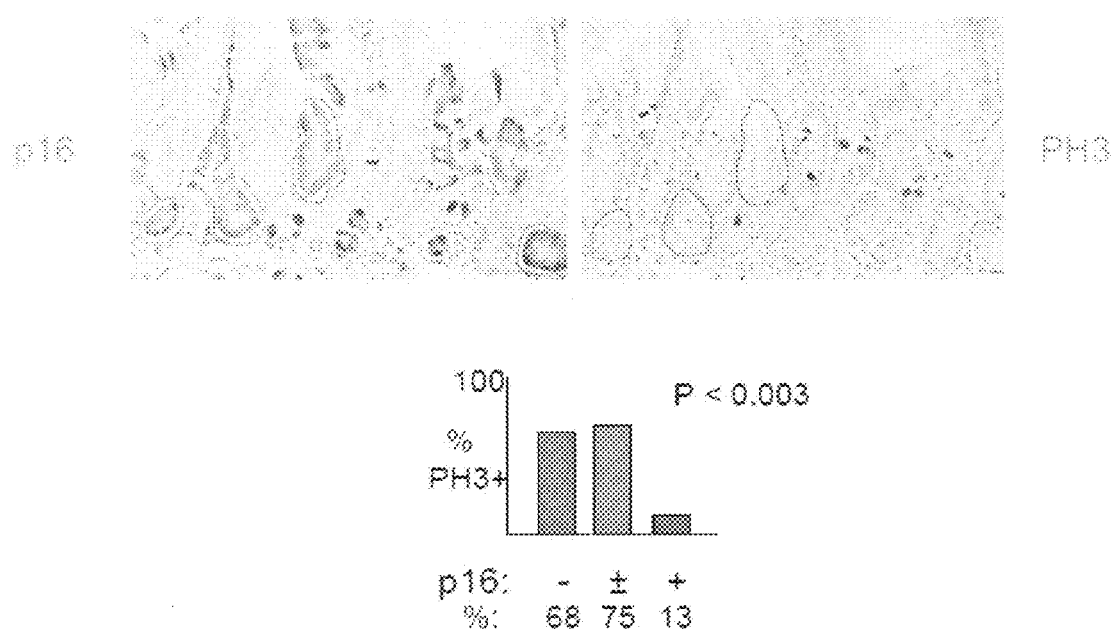

To confirm that p16 inhibited cell cycle progression rather than DNA repair, two other cell cycle markers were assayed: PCNA, another marker of S phase, and phospho-histone H3 (P-H3), a specific and robust marker of mitosis. p16 induction reduced both of these markers (FIG. 6, P<0.007 (PCNA) and P<0.003 (P-H3)).

To further rule out systemic effects as a co-factor in p16-mediated cell cycle inhibition, p16 was induced for one week using a villin-rtTA transactivator line. Consistent with previous experience with this line, p16 induction was largely confined to the intestine (data not shown). p16 induction in this setting also inhibited BrdU incorporation (data not shown). Similarly, p16 induction in skin epithelium driven by a K5-rtTA transgene inhibited PCNA staining (data not shown), providing evidence that p16 can inhibit cell proliferation in different tissues. It is believed that p16 induction is sufficient to inhibit proliferation of epithelial cells in young adult animals.

D. p16 Inhibits Intestinal Stem Cell Proliferation.

Figure 7A:
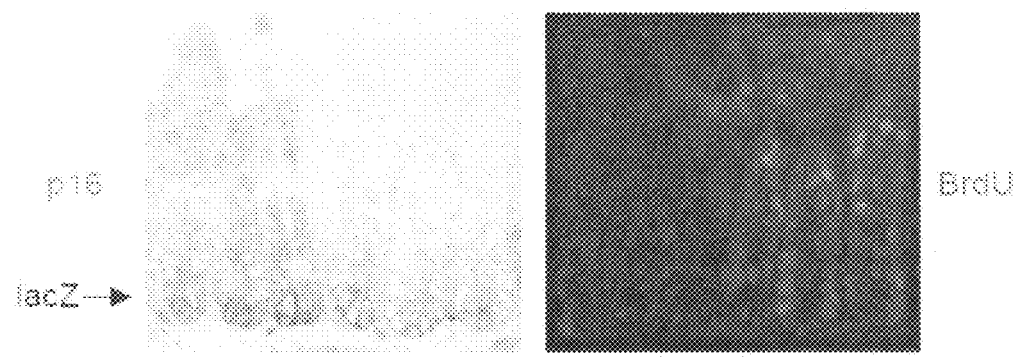
FIG. 7A) Lgr5-lacZ+:CMV-rtTA:TetO-p16 mice were treated with Dox for 1 wk and injected with BrdU 4 h before sacrifice. LacZ was detected by activity stain (left, aqua), p16 by IHC (left, brown), and BrdU by IF (right, red). Note the paucity of BrdU staining in the Lgr5-lacZ+ and p16+ cells. Across 8 20× fields, 0/331 (0%) p16+ Lgr5+ cells were BrdU+ vs. 71/461 (15%) of p16− Lgr5+ cells ($P<0.0001$ (Chi-square)).
Figure 7B:
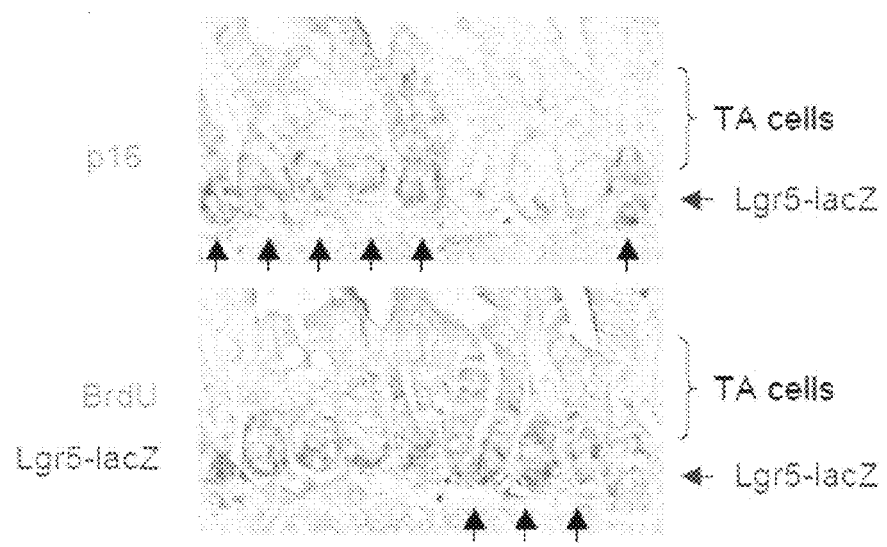
FIG. 7B) Same setting except that p16 and BrdU were each detected by IHC (brown) in serial sections. The locations of transit-amplifying cells are marked.
Figure 7C:
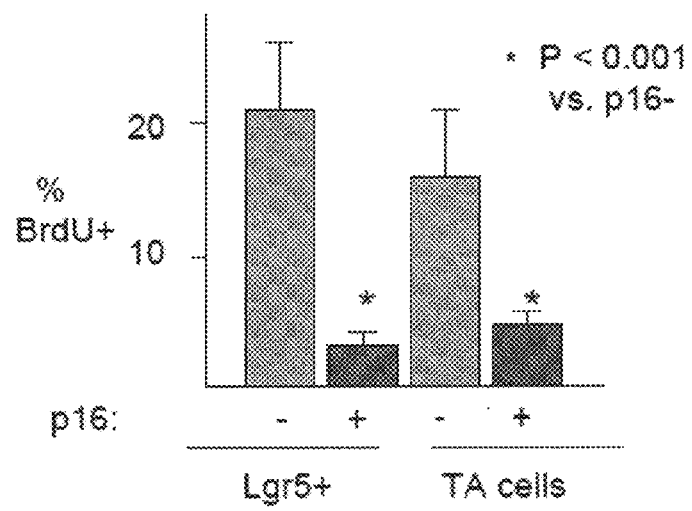
FIG. 7C) Quantitation of BrdU staining in the respective cell types by serial IHC. N=3 mice; 5,803 cells counted; random effects model.
Figure 8A:
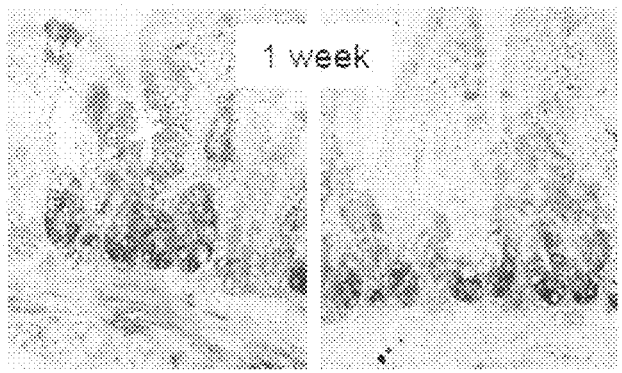
FIG. 8 shows reduced p16 expression in small intestine of mice with continuous p16 induction for 4-24 weeks. CMV-rtTA:TetO-p16 mice were treated with Dox beginning about 2 months of age and extending for 1, 4, or 2 wks. Tissue was stained for p16.
Figure 8B:
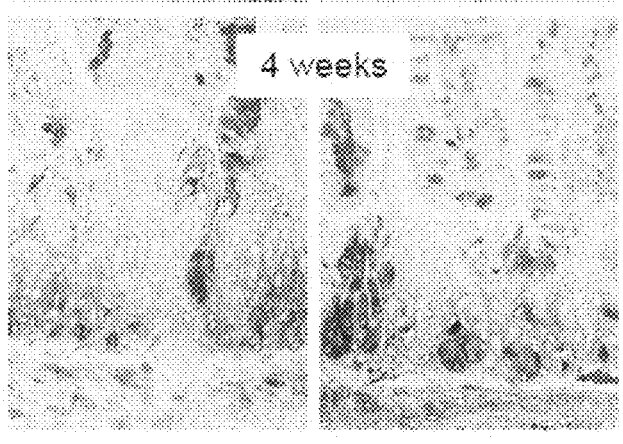
Figure 8C:
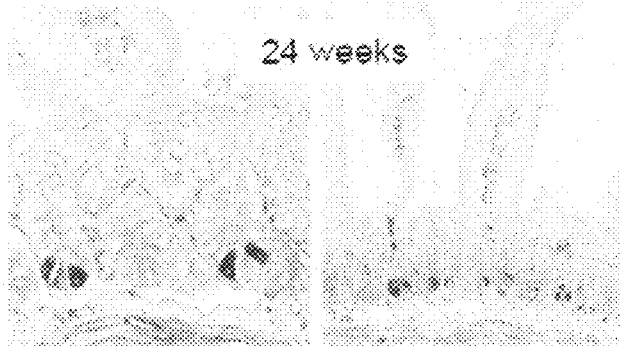

Co-staining for p16, BrdU, and β-galactosidase activity in Lgr5-lacZ mice suggested that p16 expression inhibited BrdU incorporation in TA cells and Lgr5+ stem cells (FIG. 7A). This observation was confirmed by analysis of serial sections (FIG. 7B, C; P<0.001). When p16 was continuously induced for up to 24 weeks, expression was largely lost in TA cells and villi over the first 4 weeks (FIG. 8), consistent with arrest of p16-expressing cells stem cells and regeneration of the epithelium by non-expressing cells. Serial sectioning confirmed an absence of cells with detectable p16 staining cells above p16-staining cells at the crypt base (data not shown). Staining for activated caspase 3 showed no detectable increase in apoptosis in p16-expressing tissue (data not shown), though this cannot be completely ruled out. p16 expression was largely confined to cells at or near the crypt base after 4 weeks (FIG. 8).

Figure 9A:
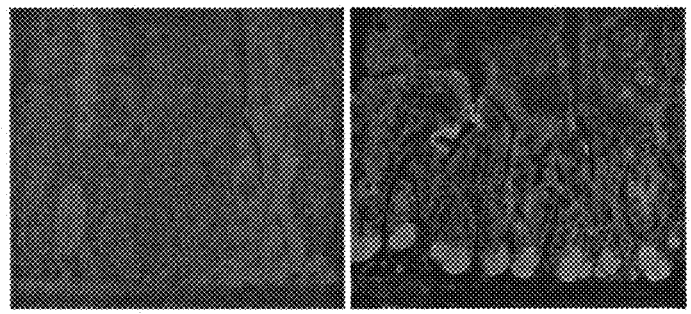
FIG. 9 shows increased co-staining of p16 and the paneth cells marker lysozyme over weeks by standard co-IF.

Co-immunofluorescence for p16 and markers of differentiation was achieved without cross-reactivity (FIG. 9A, confirmed by confocal microscopy in FIG. 11A). Following short-term induction, p16 staining was seen in all cell types, without apparent restriction (data not shown). After 4 weeks of induction, crypts with uniform p16 staining often looked atrophic (FIG. 8B, FIG. 59A, FIG. 11A, 11B). Such crypts were rare after 24 weeks (data not shown) and may die out.

Figure 9B:
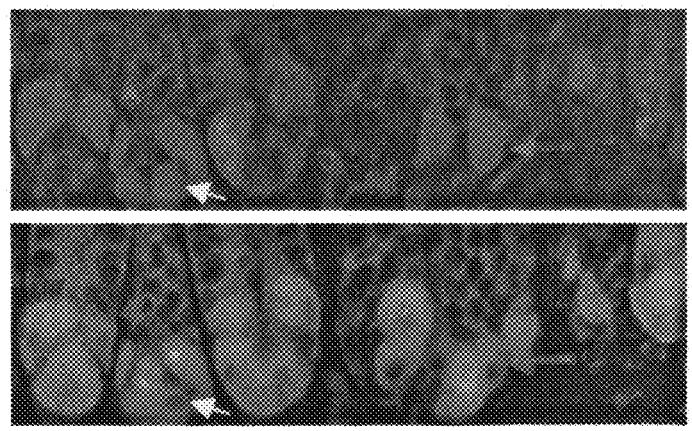
Figure 9C:
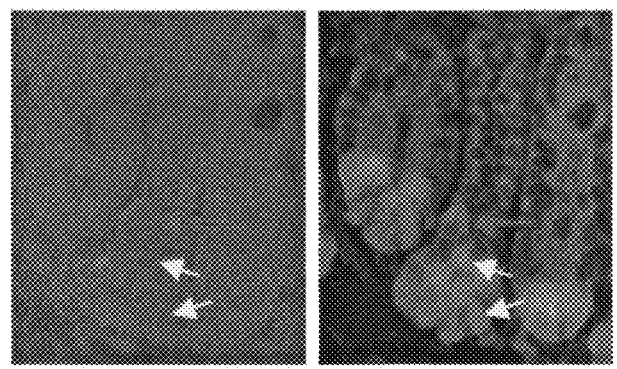

Among crypts with mosaic induction, an increasing fraction of p16-expressing cells over 4-24 weeks were found at the crypt base. Many co-stained for lysozyme, a Paneth cell marker (FIG. 9B, 9C, 9D; FIG. 11B; blue and yellow arrows). Paneth cells are non-migratory, relatively long-lived cells (ca 2 months). Thus, Paneth cells that induce p16 would be expected to persist longer than TA cells or villous cells, which typically migrate to the surface and die or are sloughed within days to weeks. However, a second factor is suggested by the observation that arrest of intestinal crypt cells mediated by conditional loss of Cdc25 cell cycle activators was associated with partial Paneth cell differentiation.

Figure 9D:
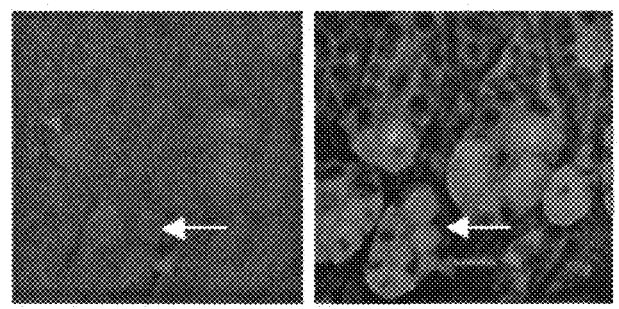

Like their adjacent Lgr5+ stem cells, Paneth cells manifest a crypt base location and Wnt pathway activation but are terminally arrested secretory cells. Neither Cdc25C inactivation nor p16 induction diminished Wnt pathway activity, as evidenced by nuclear localization of β-catenin 26 or expression of Lgr5 expression, an early Wnt target gene (data not shown). Most crypt base p16-expressing cells after 3-7 days of induction do not show lysozyme staining, arguing against widespread, acute induction of paneth cell differentiation. However, after 4 weeks of induction, p16 staining was often associated with weak lysozyme staining (FIG. 9B, 9C, 9D, FIG. 118; blue arrows), consistent with partial differentiation. On the other hand, distinct p16-expressing cells could also be found near the crypt base 8 weeks or more after induction that show no lysozyme staining (FIG. 9D, FIG. 11A; white arrows). These cells could be newly formed stem cells that induce p16. However, the more likely explanation appears to be that they are long-term arrested stem cells that do not differentiate. Some were seen in crypts with uniform p16 induction and no detectable cell proliferation (FIG. 11A, data not shown). Some p16-staining was seen in cells at the +4 position that lacked lysozyme staining, consistent with quiescent stem cells (data not shown).

Other marker studies showed no effect of p16 induction on the abundance of goblet cells or neuroendocrine cells and no co-staining for p16 and such markers following long-term induction (data not shown). In summary, these observations suggest that p16 expression is sufficient to inhibit cell cycle progression in Lgr5+ intestinal stem cells. Over many weeks, crypts with uniform p16 expression appear to die out, whereas isolated stem cells with p16 expression may remain arrested, differentiate into Paneth cells, or die.

E. p16 Induction Imposes Pre-Mature Aging Features.

Given the spontaneous alopecia in TetO-p16 mice, the ability of induced p16 to arrest normal cells, and p16's association with aging, it was asked whether p16 induction in young mice could impose pre-mature aging features. CMV-rtTA:TetO-p16 mice and singly transgenic and wild type control littermates were treated with Dox from post-natal day 20-40. This period was chosen to bracket the first wave of hair regeneration.

Dox treatment of bi-transgenic mice resulted in a distinct gross phenotype of reduced hair density over the entire coat, lower weight, and a hunched back (FIG. 10A-D). Hair density in bi-transgenic mice, quantified by shaving hair from a measured area of the back of euthanized mice, was 25% of that in the control mice (Table 1, P<0.0001). The hair was also of thinner diameter (Table 1, P<0.00001). Histological analysis revealed strong but mosaic p16 induction in skin, including Lgr5+ hair follicle stem cells (FIG. 11A).

TABLE 1

Aging features quantified following p16 induction d20-40

| | Littermate Controls | | Bi-transgenics | | | |
|---|---|---|---|---|---|---|
| | N | Mean ± SD | N | Mean ± SD | %[h] | Significance |
| Hair density[a] | 14 | 12.3 ± 1.7 | 9 | 3.1 ± 0.8 | 25 | P < 0.0001 |
| Hair diameter[b] | 3 | 1.27 ± 0.16 | 3 | 0.75 ± 0.05 | 59 | P < 0.00001 |

TABLE 1-continued

Aging features quantified following p16 induction d20-40

|  | Littermate Controls | | Bi-transgenics | | | |
|---|---|---|---|---|---|---|
|  | N | Mean ± SD | N | Mean ± SD | %[h] | Significance |
| Body weight[c] | 17 | 19.6 ± 2.5 | 8 | 17.3 ± 2.9 | 89 | P < 0.02 |
| SI length[d] | 17 | 26.9 ± 3.3 | 8 | 21.9 ± 3.6 | 81 | P < 0.002 |
| Colon length[e] | 17 | 6.0 ± 0.6 | 8 | 4.9 ± 0.7 | 82 | P < 0.0006 |
| Hematocrit[f] | 13 | 57 ± 8.4 | 8 | 53 ± 4.3 | 92 | P = 0.18 |
| Myeloid fractions[g] | 9 | 6.0 ± 6.8 | 6 | 12.8 ± 7.3 | 210 | P < 0.02 |

[a] mg/cm$^2$ shaved from mid back
[b] arbitrary units, hair shaved from mid back
[c] g, males and females combined, males alone also significantly different
[d] cm
[e] cm
[f] % packed blood cell volume
[g] % myeloid cells among white blood cells
[h] bi-transgenic value as % of control Hair follicles were in a growth phase (anagen) that was disordered, with short and long hair follicles extending into the fat layer, many devoid of hair shafts (FIG. 11B, 11C). This morphology suggests local constraints on hair follicle growth. This notion was confirmed by the observation that p16 induction for 3d at the start of hair re-growth (recognized in shaved mice) reduced PCNA labeling of hair follicle cells, before systemic effects could be detected. In addition, selective p16 induction in squamous epithelium in d20-40 shaved K5-rtTA:TetO-p16 mice markedly reduced hair regeneration (data not shown). These observations indicate that p16 expression in skin directly inhibits hair re-growth.

There was a paucity of subcutaneous and abdominal fat in CMV-rtTA-TetO-p16 mice treated with Dox d20-40. Intestines were about 18-19% shorter (P<0.002), consistent with the phenotype observed with cell cycle inhibition due to loss of Cdc25 activity. Aging humans and mice manifest a mild anemia with a shift from lymphoid to myeloid lineages. There was a trend toward mild anemia in the bi-transgenic mice (Table 1). Peripheral blood smears revealed a myeloid shift (P<0.02). These observations suggest that p16 induction is sufficient to impose some features of aging.

Figures 10A, 10B, 10C, 10D, 10E, 10F:
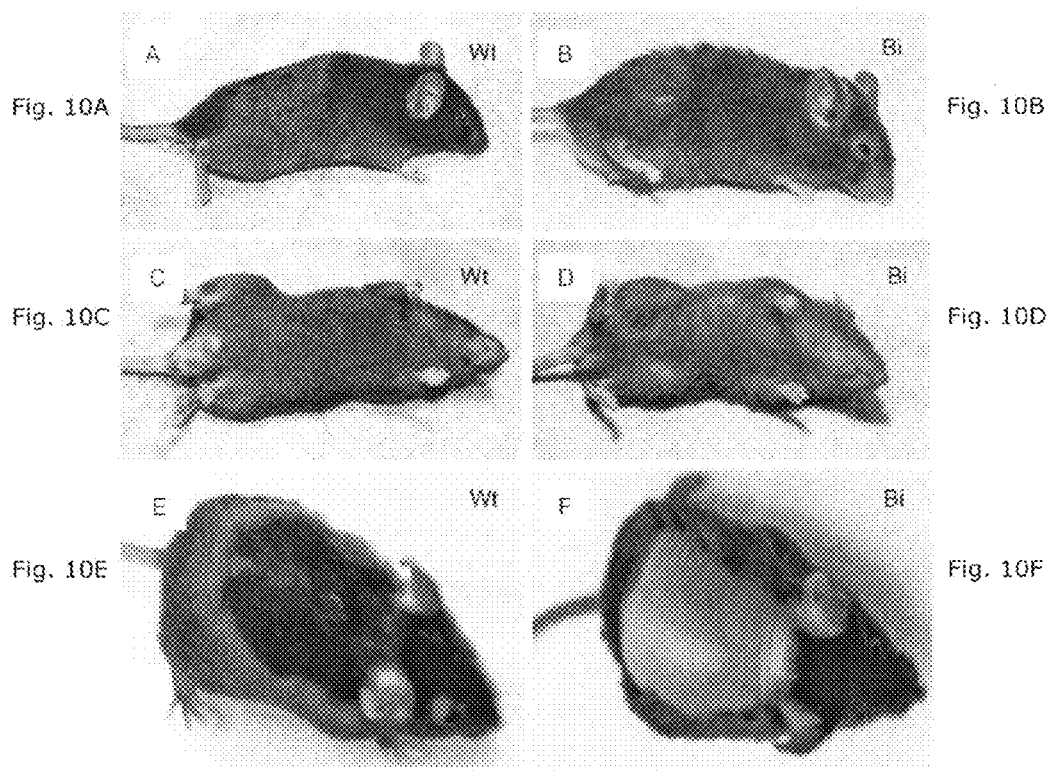
FIG. 10 shows p16 induction d20-40 in CMV-rtTA-TetO-p16 mice inhibits hair regeneration. Bi-transgenic (Bi) mice (B, D, F) and wild type (Wt; A, C, E) littermates were treated with Dox d20-40. Bi-transgenic mice showed reduced hair density over the entire coat, including the dorsum/back (B) and ventral/underbelly (D). Other mice were shaved of back hair at d26 (E, F). Robust hair re-growth occurred by d36 in Wt (E) but not Bi-transgenic mice (F).

To test directly whether the reduced hair density on bi-transgenic mice represented inhibition of hair growth or accelerated hair loss, mice treated with Dox from d20 were shaved of back hair at d26. The bi-transgenic mice consistently showed markedly delayed and reduced hair growth (FIG. 10E, 10F). This finding confirms that the bi-transgenic mice are defective in hair regeneration.

F. The Pre-Mature Aging Features are Reversible.

It was then asked whether sustained p16 induction would sustain and/or further compromise tissue structure and function and, in contrast, whether these phenotypes might revert upon Dox withdrawal. If p16 imposes senescence in most of its target cells, with an irreversible block to cell proliferation, then the imposed features of tissue dysfunction might be irreversible. In addition, tissue compromise might become self-sustaining, potentially without irreversible and cell-autonomous loss of cell proliferation, if it, e.g., sufficiently compromised stroma supports or key paracrine and/or hormonal growth signaling.

Following Dox treatment d20-40 in bi-transgenic mice, the animals were divided into two groups. Dox was continued in the first group and withdrawn in the second. Hair was shaved from the backs of some mice at d40, to allow specific scrutiny of hair regeneration. The mice were euthanized at d80.

Figure 12A:
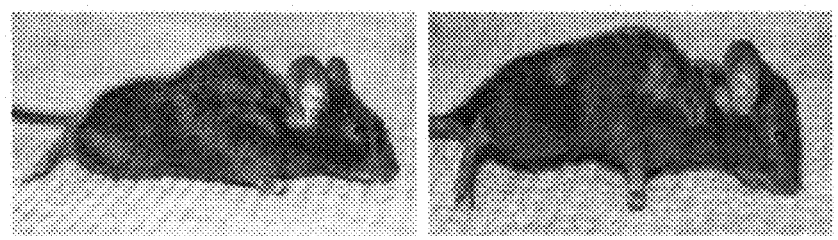
FIG. 12A) Sustained Dox treatment d20-80 results in persistent growth defects. Note the thin hair, hunched posture, thin body, and sunken eyes.
Figure 12B:
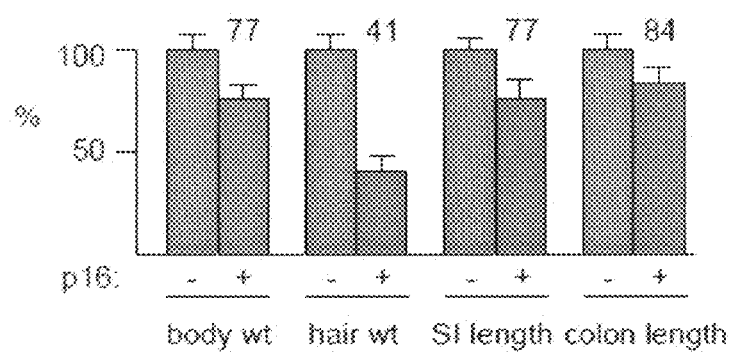
FIG. 12B) Body weight, back hair density (weight/$cm^2$), SI and colon length in bi-transgenic mice (N=8) were measured and normalized to that of their non-bi-transgenic littermates (mean, ±SD; N=6).
Figure 12C:
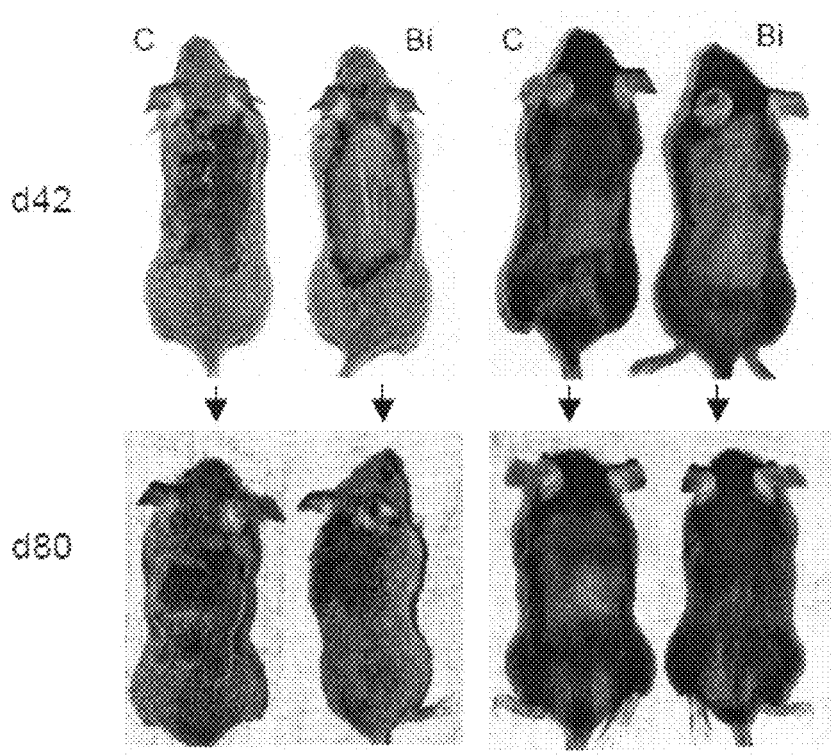
FIG. 12C) Bi-transgenic (Bi) and control mice (C) were treated with Dox d20-40, shaved of back hair on d40, and photographed on d42 and d80. Note that hair re-grew robustly on the bi-transgenic mice by d80 following Dox withdrawal.
Figure 13A:
FIG. 13 shows hair follicle growth trapped in anagen by p16 induction.
Figure 13B:
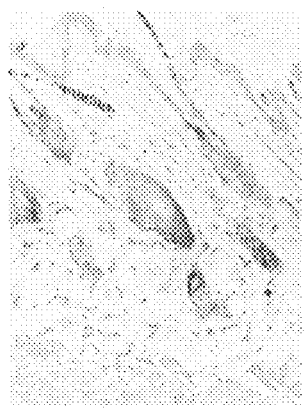
Figure 13C:

Sustained Dox treatment was associated with persistently reduced hair density and body weight (FIG. 12A, 12B). Histological analysis of skin continued to show a disordered anagen (FIG. 13). Some mice developed malocclusion of the incisors (FIG. 12A) whereas others showed loss of most of the incisors, with only tooth stubs remaining (not shown). Some bi-transgenic mice approached a criteria for euthanasia, based on reduced spontaneous movements, persistent hunched posture, and decreased grooming, and one died before it could be euthanized. In contrast, when Dox was withdrawn at d40, hair re-grew, often more robustly than in wild type or singly transgenic littermates (FIG. 12C). Weight, intestine length, and myeloid/lymphoid ratio also normalized, and the mice demonstrated normal foraging and grooming behavior. These observations indicate that the pre-mature aging features imposed by p16 were largely reversible.

To rule out the possibility that the observed features were dependent on mutation at the integration site of the rtTA transactivator, the experiments were repeated using an ROSA-M2-rtTA transactivator line. This line also yields broad p16 induction, particularly in intestine, skin, and bone marrow (FIG. 14A, 14B). Dox treatment d20-80 yielded marked hair loss with loss of subcutaneous fat and wrinkling (FIG. 14C).

G. p16 Induction Reduces Intestinal Tumor Formation.

Figure 16:
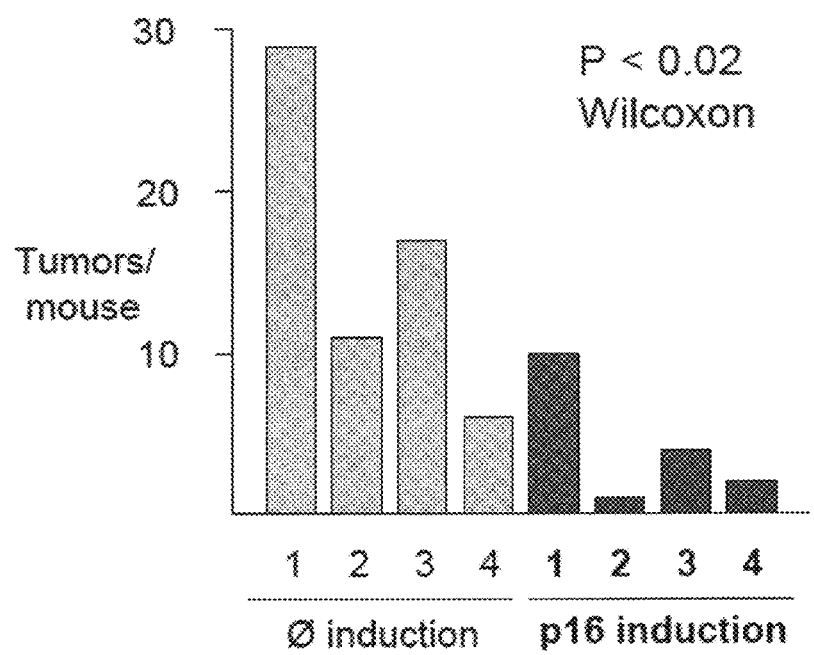
FIG. 16 shows intestinal tumors are reduced in multiple intestinal neoplasia mice in which the p16 transgene was induced, relative to multiple intestinal neoplasia mice in which the p16 transgene was not induced.

Two groups of Multiple intestinal neoplasia mice (for each group, n=4) were screened for tumor formation in the small and large intestines. The first group was transgenic for the CMV-rtTA transactivator alone. The second group was transgenic for both the transactivator and TetO-p16. Dox was administered to both groups continuously from approximately six weeks of age. At approximately 6 months of age, the mice were analyzed for the number of tumors and the volume of the tumors in their intestines. As shown in FIG. 16, the bi-transgenic mice, in which p16 was induced, had significantly fewer intestinal tumors relative to their counterparts in which the transgene was not induced. Relatedly, p16-induced mice also demonstrated an approximately 90% reduction in tumor volume (data not shown). These results suggest an active tumor suppression function for the p16 transgene in the Min mice.

EXAMPLE 3

Summary

A. Transgenic Mice.

TetO-p16 transgenic mice allow inducible expression of a potent cell cycle inhibitor, p16lnk4a. In the transgene, the human p16 cDNA was positioned behind multimerized operons that can bind the reverse tetracycline transactivator (rtTA, or similar proteins), mediating p16 transcription.

TetO-p16 mice can be mated to mice carrying rtTA transgenes that are expressed in all or a subset of tissues. Doubly transgenic mice can be administered the well-tolerated antibiotic doxycycline in the drinking water or chow, thereby mediating facile induction of p16 in pre-determined target tissue at the time and for the duration chosen by the investigator.

p16 inhibits cell proliferation in each of the tissues studied. Initial experiments suggest that global p16 induction may impose an early aging phenotype. Potential applications include studies of development, tissue regeneration, aging, cancer, and other chronic diseases involving cell proliferation.

B. p16 Function Begins in Normal Cells of Young Animals.

Expression of mouse p16 in intestinal epithelium mirrors the patterns seen in human intestine in normal and disease states, with preferential expression in Lgr5+ stem cells at the base of crypts. The expression is typically patchy, consistent with the notion that p16 constrains cell proliferation of subsets of stem cells and their immediate progeny that develop replicative stress. In preliminary support of this notion, p16-null epithelial cells demonstrate increased markers of replicative stress (data not shown).

C. Interphase Cdks are Needed for Normal Postnatal Tissue Homeostasis

The data suggest that the effects of p16 depend on binding to Cdk4 and that Cdk4/6/2 activity is needed for post-natal tissue homeostasis. Results of constitutive knockouts indicate that none of these kinases is absolutely essential in the mouse. However, in their absence, Cdk1 can bind interphase cyclins and fulfill the activities of the absent kinases. p16 is a specific Cdk 4/6 binding partner and can only inhibit Cdk2 indirectly. It is possible that Cdk4/6/2 are essential proteins when expressed and bound to their normal cyclin partners. It is important for the prospects of drug targeting of Cdks, e.g., for cancer therapy, cancer chemoprevention, or treatment of auto-immune disease. Inhibition of interphase Cdks may potently block cell proliferation, even though none are strictly essential. Thus, the p16-inducible mouse described herein offers a test of the need for interphase Cdk activity and models the potential effects of a selective interphase Cdk inhibitor.

D. p16 is an Effector of Aging.

The data indicate that p16 can contribute to aging features, at least at the levels expressed here. Endogenous p16 does not impose all these features at an early age. Rather, the results demonstrate the potential for Cdk inhibition and inhibition of cell proliferation, more broadly, to cause aging features. Aging is complex. It is associated with various types of macromolecular damage, cell death, and loss of proliferative capacity. The effects of p16 suggest that inhibition of cell proliferation is sufficient to account for some aging features.

The invention is not limited to the embodiments described and exemplified above, but is capable of variation and modification within the scope of the appended claims.

I claim:

1. A transgenic mouse, comprising a p16(Ink4a) transgene comprising an inducible promoter operably linked to a p16(Ink4a) gene consisting of the nucleic acid sequence of SEQ ID NO:14.

2. The transgenic mouse of claim 1, wherein the inducible promoter is activated by the reverse tetracycline-controlled transactivator.

3. The transgenic mouse of claim 1, wherein the transgene is stably integrated into a chromosome.

4. The transgenic mouse of claim 1, wherein following induction, the p16(Ink4a) transgene is expressed in the skin of the mouse.

5. The transgenic mouse of claim 1, wherein following induction, the p16(Ink4a) transgene is expressed in a gastrointestinal tissue of the mouse.

6. The transgenic mouse of claim 5, wherein the gastrointestinal tissue is the tongue, esophagus, stomach, small intestine, or large intestine of the mouse.

7. A cell isolated from the transgenic mouse of claim 1, wherein the cell comprises the transgene.

8. A tissue isolated from the transgenic mouse of claim 1, wherein at least one cell in the tissue comprises the transgene.

9. An organ isolated from the transgenic mouse of claim 1, wherein at least one cell in the organ comprises the transgene.

10. A method for producing the transgenic mouse of claim 1, comprising introducing a nucleic acid sequence comprising an inducible promoter operably linked to a p16(Ink4a) gene consisting of the nucleic acid sequence of SEQ ID NO:14 into a mouse egg, embryo, or embryonic stem cell, and transferring the mouse egg, embryo, or embryonic stem cell having the introduced nucleic acid sequence into a female mouse.

11. The method of claim 10, further comprising breeding the female mouse and selecting offspring having the nucleic acid sequence.

12. A method for producing the transgenic mouse of claim 1, comprising introducing a p16(Ink4a) transgene comprising an inducible promoter operably linked to a p16(Ink4a) gene consisting of the nucleic acid sequence of SEQ ID NO:14 into a mouse egg, embryo, or embryonic stem cell; transferring the mouse egg, embryo, or embryonic stem cell having the introduced p16(Ink4a) transgene into a female mouse, breeding the female mouse with a male mouse comprising a reverse tetracycline transactivator transgene; and selecting offspring having the p16(Ink4a) transgene and the reverse tetracycline transactivator transgene.

13. The method of claim 12, wherein the inducible promoter is operably linked to an operon capable of activation by the reverse tetracycline transactivator.

14. The method of claim 13, wherein the operon is a single operon or a multimeric operon.

15. A mouse produced by the method of claim 10.

16. A mouse produced by the method of claim 12.

17. A method for inducing p16 expression in the transgenic mouse of claim 1, comprising administered to the mouse an agent capable of activating the inducible promoter.

18. The method of claim 17, wherein the inducible promoter is activated by the reverse tetracycline-controlled transactivator.

19. The method of claim 17, wherein the agent comprises tetracycline or a tetracycline analog.

20. The method of claim 19, wherein the analog comprises doxycycline.

21. The method of claim 17, wherein the agent is selectively administered to a tissue of interest.

22. A method for producing the transgenic mouse of claim 1, comprising breeding a mouse comprising a p16(Ink4a) transgene comprising an inducible promoter operably linked to a p16(Ink4a) gene consisting of the nucleic acid sequence of SEQ ID NO:14 with a mouse comprising a reverse tetracycline transactivator transgene, and selecting offspring having the p16(Ink4a) transgene and the reverse tetracycline transactivator transgene.

23. A mouse produced by the method of claim 22.

* * * * *

SEQUENCE LISTING

```
<160> NUMBER OF SEQ ID NOS: 15

<210> SEQ ID NO 1
<211> LENGTH: 670
<212> TYPE: DNA
<213> ORGANISM: Homo sapiens

<400> SEQUENCE: 1
ttcgagctcg gtaccgggga tccagcatgg accccgccgc cggctccagc atggagcctt      60
cggctgactg gctggccacg gccgcggccc ggggtcgggt agaggaggtg cgggcgctgc     120
tggaggcggg ggcgctgccc aacgcaccga atagttacgg tcggaggccg atccaggtca     180
tgatgatggg cagcgcccga gtggcggagc tgctgctgct ccacggcgcg gagcccaact     240
gcgccgaccc cgccactctc acccgacccg tgcacgacgc tgcccgggag ggcttcctgg     300
acacgctggt ggtgctgcac cgggccgggg cgcggctgga cgtgcgcgat gcctggggcc     360
gtctgcccgt ggacctggct gaggagctgg gccatcgcga tgtcgcacgg tacctgcgcg     420
cggctgcggg gggcaccaga ggcagtaacc atgcccgcat agatgccgcg gaaggtccct     480
cagacatccc cgattgaaag ggatccagac atgataagat acattgatga gtttggacaa     540
accacaacta gaatgcagtg aaaaaaatgc tttatttgtg aaatttgtga tgctattgct     600
ttatttgtaa ccattataag ctgcaataaa caagttaaca acaacaattg cattcatttt     660
atgtttcagg                                                           670

<210> SEQ ID NO 2
<211> LENGTH: 20
<212> TYPE: DNA
<213> ORGANISM: Artificial Sequence
<220> FEATURE:
<223> OTHER INFORMATION: Completely Synthesized

<400> SEQUENCE: 2
atccacgctg ttttgacctc                                                 20

<210> SEQ ID NO 3
<211> LENGTH: 20
<212> TYPE: DNA
<213> ORGANISM: Artificial Sequence
```

```
<220> FEATURE:
<223> OTHER INFORMATION: Completely Synthesized

<400> SEQUENCE: 3
ggcctccgac cgtaactatt                                          20

<210> SEQ ID NO 4
<211> LENGTH: 20
<212> TYPE: DNA
<213> ORGANISM: Artificial Sequence
<220> FEATURE:
<223> OTHER INFORMATION: Completely Synthesized

<400> SEQUENCE: 4
cgtaactatt cggtgcgttg                                          20

<210> SEQ ID NO 5
<211> LENGTH: 6
<212> TYPE: DNA
<213> ORGANISM: Klebsiella pneumoniae

<400> SEQUENCE: 5 ggtacc                                                          6

<210> SEQ ID NO 6
<211> LENGTH: 6
<212> TYPE: DNA
<213> ORGANISM: Bacillus amyloliquefaciens

<400> SEQUENCE: 6 ggatcc                                                          6

<210> SEQ ID NO 7
<211> LENGTH: 14
<212> TYPE: DNA
<213> ORGANISM: Artificial Sequence
<220> FEATURE:
<223> OTHER INFORMATION: Completely Synthesized

<400> SEQUENCE: 7
agcatggagc cttc                                                14

<210> SEQ ID NO 8
<211> LENGTH: 19
<212> TYPE: DNA
<213> ORGANISM: Artificial Sequence
<220> FEATURE:
<223> OTHER INFORMATION: Completely Synthesized

<400> SEQUENCE: 8
gatccaggtc atgatgatg                                           19

<210> SEQ ID NO 9
<211> LENGTH: 20
<212> TYPE: DNA
<213> ORGANISM: Artificial Sequence
<220> FEATURE:
<223> OTHER INFORMATION: Completely Synthesized

<400> SEQUENCE: 9
aatagttacg gtcggaggcc                                          20

<210> SEQ ID NO 10
<211> LENGTH: 10
<212> TYPE: DNA
<213> ORGANISM: Artificial Sequence
```

```
<220> FEATURE:
<223> OTHER INFORMATION: Completely Synthesized

<400> SEQUENCE: 10
caacgcaccg                                                              10

<210> SEQ ID NO 11
<211> LENGTH: 21
<212> TYPE: DNA
<213> ORGANISM: Artificial Sequence
<220> FEATURE:
<223> OTHER INFORMATION: Completely synthesized

<400> SEQUENCE: 11
agctcgttta gtgaaccgtc a                                                 21

<210> SEQ ID NO 12
<211> LENGTH: 20
<212> TYPE: DNA
<213> ORGANISM: Artificial Sequence
<220> FEATURE:
<223> OTHER INFORMATION: Completely synthesized

<400> SEQUENCE: 12
cctccgaccg taactattcg                                                   20

<210> SEQ ID NO 13
<211> LENGTH: 1267
<212> TYPE: DNA
<213> ORGANISM: Homo sapiens

<400> SEQUENCE: 13
cgagggctgc ttccggctgg tgccccgggg ggagacccaa cctggggcga cttcaggggt        60
gccacattcg ctaagtgctc ggagttaata gcacctcctc cgagcactcg ctcacggcgt       120
ccccttgcct ggaaagatac cgcggtccct ccagaggatt tgaggacag ggtcggaggg        180
ggctcttccg ccagcaccgg aggaagaaag aggagggct ggctggtcac cagagggtgg       240
ggcggaccgc gtgcgctcgg cggctgcgga gaggggaga gcaggcagcg ggcggcgggg       300
agcagcatgg agccggcggc ggggagcagc atggagcctt cggctgactg gctggccacg      360
gccgcggccc ggggtcgggt agaggaggtg cgggcgctgc tggaggcggg ggcgctgccc      420
aacgcaccga atagttacgg tcggaggccg atccaggtca tgatgatggg cagcgcccga      480
gtggcggagc tgctgctgct ccacggcgcg gagcccaact cgccgacccc gccactctc      540
acccgacccg tgcacgacgc tgcccgggag ggcttcctgg acacgctggt ggtgctgcac      600
cgggccgggg cgcggctgga cgtgcgcgat gcctgggcc gtctgcccgt ggacctggct      660
gaggagctgg gccatcgcga tgtcgcacgg tacctgcgcg cggctgcggg gggcaccaga      720
ggcagtaacc atgcccgcat agatgccgcg gaaggtccct cagacatccc cgattgaaag      780
aaccagagag gctctgagaa acctcgggaa acttagatca tcagtcaccg aaggtcctac      840
agggccacaa ctgccccgc cacaacccac cccgctttcg tagttttcat ttagaaaata      900
gagcttttaa aaatgtcctg ccttttaacg tagatatatg ccttcccca ctaccgtaaa      960
tgtccattta tatcattttt tatatattct tataaaaatg taaaaagaa aaacaccgct     1020
tctgcctttt cactgtgttg gagttttctg gagtgagcac tcacgcccta agcgcacatt     1080
catgtgggca tttcttgcga gcctcgcagc ctccggaagc tgtcgacttc atgacaagca     1140
ttttgtgaac tagggaagct caggggggtt actggcttct cttgagtcac actgctagca     1200
aatggcagaa ccaaagctca aataaaaata aaataatttt cattcattca ctcaaaaaaa     1260
```

-continued aaaaaaa                                                                1267

<210> SEQ ID NO 14
<211> LENGTH: 451
<212> TYPE: DNA
<213> ORGANISM: Homo sapiens

<400> SEQUENCE: 14
gagggtgggg cggaccgcgt gcgctcggcg gctgcggaga gggggagagc aggcagcggg      60
cggcggggag cagcatggag ccggcggcgg ggagcagcat ggagccttcg gctgactggc     120
tggccacggc cgcggcccgg ggtcgggtag aggaggtgcg ggcgctgctg gaggcggggg     180
cgctgcccaa cgcaccgaat agttacggtc ggaggccgat ccaggtcatg atgatgggca     240
gcgcccgagt ggcggagctg ctgctgctcc acggcgcgga gcccaactgc gccgaccccg     300
ccactctcac ccgacccgtg cacgacgctg cccgggaggg cttcctggac acgctggtgg     360
tgctgcaccg ggccggggcg cggctggacg tgcgcgatgc ctggggccgt ctgcccgtgg     420
acctggctga ggagctgggc catcgcgatg t                                    451

<210> SEQ ID NO 15
<211> LENGTH: 1437
<212> TYPE: DNA
<213> ORGANISM: Homo sapiens

<400> SEQUENCE: 15
ctcctccgag cactcgctca cggcgtcccc ttgcctggaa agataccgcg gtccctccag      60
aggatttgag ggacagggtc ggagggggct cttccgccag caccggagga agaaagagga    120
ggggctggct ggtcaccaga gggtggggcg gaccgcgtgc gctcggcggc tgcggagagg    180
gggagagcag gcagcgggcg gcggggagca gcatggagcc ggcggcgggg agcagcatgg    240
agccttcggc tgactggctg ccacggccg cggcccgggg tcgggtagag gaggtgcggg     300
cgctgctgga ggcgggggcg ctgcccaacg caccgaatag ttacggtcgg aggccgatcc    360
aggtgggtag agggtctgca gcgggagcag gggatggcgg gcgactctgg aggacgaagt    420
ttgcagggga attggaatca ggtagcgctt cgattctccg gaaaaagggg aggcttcctg    480
gggagttttc agaagggggtt tgtaatcaca gacctcctcc tggcgacgcc ctgggggctt    540
gggaagccaa ggaagaggaa tgaggagcca cgcgcgtaca gatctctcga atgctgagaa    600
gatctgaagg ggggaacata tttgtattag atggaagtca tgatgatggg cagcgcccga    660
gtggcggagc tgctgctgct ccacggcgcg gagcccaact gcgccgaccc cgccactctc    720
acccgacccg tgcacgacgc tgcccgggag ggcttcctgg acacgctggt ggtgctgcac    780
cgggccgggg cgcggctgga cgtgcgcgat gcctggggcc gtctgcccgt ggacctggct    840
gaggagctgg gccatcgcga tgtcgcacg tacctgcgcg cggctgcggg ggcaccaga     900 ggcagtaacc atgcccgcat agatgccgcg gaaggtccct cagacatccc cgattgaaag    960
aaccagagag gctctgagaa acctcgggaa acttagatca tcagtcaccg aaggtcctac   1020
agggccacaa ctgcccccgc cacaacccac cccgctttcg tagttttcat ttagaaaata   1080
gagcttttaa aaatgtcctg ccttttaacg tagatatatg ccttcccca ctaccgtaaa    1140 tgtccattta tatcatttt tatatattct tataaaaatg taaaaagaa aaacaccgct      1200 tctgcctttt cactgtgttg gagttttctg gagtgagcac tcacgccta agcgcacatt    1260 catgtgggca tttcttgcga gcctcgcagc ctccggaagc tgtcgacttc atgacaagca   1320

```
ttttgtgaac tagggaagct caggggggtt actggcttct cttgagtcac actgctagca    1380
aatggcagaa ccaaagctca aataaaaata aaataatttt cattcattca ctcaaaa       1437
```